United States Patent
Friedman et al.

(10) Patent No.: US 9,186,103 B2
(45) Date of Patent: Nov. 17, 2015

(54) SYSTEM AND METHOD FOR SPIN LOGIC

(71) Applicant: Northwestern University, Evanston, IL (US)

(72) Inventors: Joseph S. Friedman, Rochester, NY (US); Bruce W. Wessels, Wilmette, IL (US); Alan V. Sahakian, Northbrook, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/297,882

(22) Filed: Jun. 6, 2014

(65) Prior Publication Data

US 2014/0361808 A1    Dec. 11, 2014

Related U.S. Application Data

(60) Provisional application No. 61/833,622, filed on Jun. 11, 2013.

(51) Int. Cl.
| | |
|---|---|
| *H03K 19/173* | (2006.01) |
| *A61B 5/1459* | (2006.01) |
| *A61B 5/1473* | (2006.01) |
| *A61B 17/00* | (2006.01) |
| *A61B 19/00* | (2006.01) |
| *G01N 21/25* | (2006.01) |
| *G01J 3/02* | (2006.01) |

(52) U.S. Cl.
CPC ............. *A61B 5/1459* (2013.01); *A61B 5/1473* (2013.01); *A61B 17/00234* (2013.01); *A61B 19/2203* (2013.01); *G01N 21/255* (2013.01); *H03K 19/1735* (2013.01); *A61B 2019/2215* (2013.01); *G01J 3/0224* (2013.01); *G01N 2201/06113* (2013.01)

(58) Field of Classification Search
CPC ............................ H03K 19/1735; G06F 7/501
USPC ............................................ 326/38, 104, 135
See application file for complete search history.

(56) References Cited

U.S. PATENT DOCUMENTS

| | | | |
|---|---|---|---|
| 2008/0180857 A1* | 7/2008 | Takahashi et al. | ............ 360/313 |
| 2010/0105834 A1 | 4/2010 | Tour et al. | |
| 2011/0115522 A1* | 5/2011 | Javerliac et al. | ................ 326/35 |
| 2013/0063178 A1* | 3/2013 | Friedman et al. | ................ 326/41 |
| 2013/0223166 A1* | 8/2013 | Schuette | ................ 365/189.16 |
| 2014/0002137 A1 | 1/2014 | Friedman et al. | |

OTHER PUBLICATIONS

Santos, H., et al. "Carbon nanoelectronics: unzipping tubes into graphene ribbons." Phys. Rev. Lett. 103, 086801 (2009).
Bai, J., et al. "Very large magnetoresistance in graphene nanoribbons." Nature Nanotech. 5, 655-659 (Sep. 2010).

* cited by examiner

*Primary Examiner* — Don Le
(74) *Attorney, Agent, or Firm* — Klintworth & Rozenblat IP LLC (57) ABSTRACT

Systems and methods can perform automatic computation developed using carbon nanotubes and graphene nanoribbons and/or InSb p-n bilayer channel avalanche diodes and wires. Spin logic can provide improvements in speed, power, and area, promising to be a high-performance logic family for the next generation of computing. The systems and methods can replace CMOS, for example, for general computing applications.

18 Claims, 6 Drawing Sheets

SYSTEM AND METHOD FOR SPIN LOGIC

CROSS-REFERENCE TO RELATED APPLICATIONS

This application claims the benefit of U.S. Provisional Application Ser. No. 61/833,622, filed Jun. 11, 2013, the entire contents of which are incorporated by reference herein.

FIELD

The embodiments relates generally to electronic switching systems and methods for performing automatic computation developed using carbon nanotubes and graphene nanoribbons from all-carbon spin logic systems and/or using an InSb p-n bilayer channel avalanche diode and wires.

BACKGROUND

Graphene, carbon nanotubes (CNTs), and spintronic logic have been suggested as replacements to silicon complementary logic as transistor scaling approaches its inherent limits. Carbon nanotube (CNT) and graphene nanoribbon (GNR) logic circuits have been fabricated for the conventional complementary metal-oxide-semiconductor (CMOS) logic family that take advantage of the fast switching speeds and high current density of low-dimensional carbon materials. Additionally, new logic families are enabled by spintronics, in which electron spin is manipulated along with electron charge to perform logical functions efficiently. Large leakage currents in graphene transistors have inhibited their use in the CMOS logic family, and spintronic circuit development has been hampered by the difficulty in cascading logic gates.

BRIEF DESCRIPTION OF DRAWINGS

Comprehension of the systems and methods is facilitated by reading the following detailed description, in conjunction with the annexed drawing, in which.

DETAILED DESCRIPTION

Continued reduction in transistor sizes has provided the technological basis for marked circuit performance improvements, making possible billion transistor integrated circuits operating at gigahertz frequencies. The smaller size of these devices, however, results in increased fabrication difficulties, higher power densities, and parasitic effects that threaten to limit the further improvement of Si-based circuits. In an effort to provide continued improvements in computing performance, newly available materials and devices are evaluated as building blocks for next generation computing.

Computing systems and methods described herein can operate with greater efficiency than CMOS computing arrangements. Logic systems and method are not subject to the leakage currents that have plagued graphene transistors and that have inhibited their use in the CMOS logic family. The systems and methods can perform automatic computation using carbon nanotubes and graphene. The systems and methods can perform automatic computation using carbon nanotubes and graphene transistors that readily can be cascaded as logic gates. The systems and methods can perform automatic computation that can be scaled beyond the inherent limits of silicon complementary logic. The systems and methods can perform automatic computation wherein electron spin can be manipulated to perform logic functions. The systems and methods can perform automatic computation wherein the number of transistors per logic function block is reduced over that required in conventional implementations.

Figure 1:
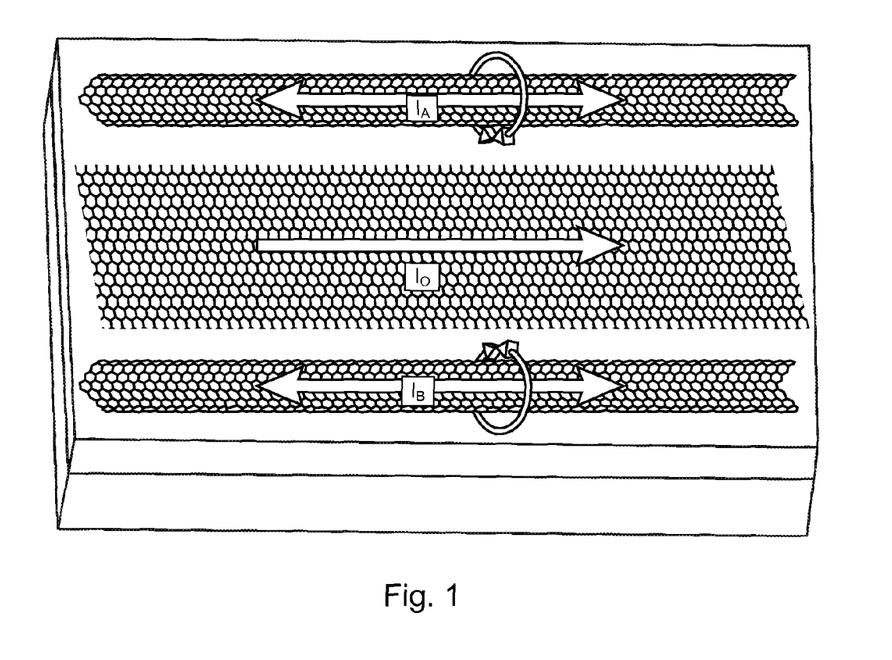
FIG. 1 is an exemplary representation of a spin logic OR/XOR basis gate.

FIG. 1 is an exemplary representation of a basic logic element in a spin logic OR/XOR basis gate. In one implementation, the spin logic can be all-carbon. A spintronic graphene nanoribbon (GNR) gate (shown with a single-headed arrow thereon) is controlled by two carbon nanotubes (CNTs) (each shown with a two-headed arrow thereon) that are disposed in the figure parallel to the GNR on an insulating material that is grown on a metallic gate. As voltages are held constant, the input currents IA and IB are unidirectional.

The spin logic OR/XOR gate shown in FIG. 1 has four regions of operation:

I) No current flows through either CNT control wire: there is no magnetic field perpendicular to the graphene layer, causing the GNR to operate in its resistive state. Minimal current therefore flows through the GNR.

II) Current flows through one CNT control wire: there is a large magnetic field perpendicular to the graphene layer, causing the GNR to operate in its conductive state. A large current therefore flows through the GNR.

III) Current flows through both CNT control wires in parallel directions and of equal magnitude: the magnetic fields through the graphene layer are anti-parallel, resulting in cancellation of the magnetic fields. The GNR therefore operates in its resistive state, and minimal current flows through the GNR.

IV) Current flows through both CNT control wires in anti-parallel directions: the magnetic fields through the graphene layer are parallel, resulting in a doubly large magnetic field. The GNR therefore operates in its conductive state, and a large current will flow through the GNR.

As voltages are constant, the current directions are determined. Therefore, an OR gate is determined by control currents oriented in anti-parallel directions, permitting regions of operation I, II, and IV as shown in Table 1. Similarly, an XOR gate is determined by control currents oriented in parallel directions, as shown in Table 2.

The OR gate truth table and regions of operation for parallel input currents IA and IB and output current Io is shown in Table 1:

TABLE 1

OR Gate Truth Table

| $I_A$ | $I_B$ | Operating Region | $I_O$ |
|---|---|---|---|
| 0 | 0 | I | 0 |
| 0 | −I | II | I |
| +I | 0 | II | I |
| +I | −I | IV | I |

The XOR gate truth table for anti-parallel input currents is shown in Table 2:

TABLE 2

XOR Gate Truth Table

| $I_A$ | $I_B$ | Operating Region | $I_O$ |
|---|---|---|---|
| 0 | 0 | I | 0 |
| 0 | −I | II | I |
| +I | 0 | II | I |
| +I | +I | III | 0 |

Figure 2:
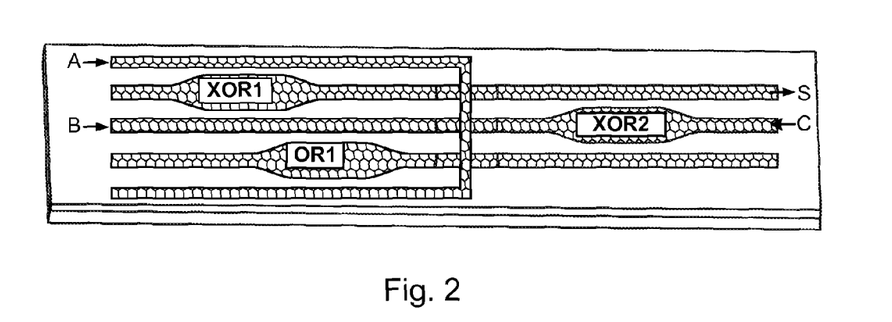
FIG. 2 is an exemplary representation of a half adder using spin logic.

FIG. 2 is an exemplary representation of a half adder that uses spin logic. CNTs are partially unzipped to create GNRs with negative magnetoresistance that perform the half adder logic function. CNT input currents A and B are connected to the output of a GNR elsewhere in the circuit, and flow in parallel alongside XOR1 to compute A⊕B, which is output as sum S. Current A crosses over insulated (brown) CNTs without making an electrical connection, flowing opposite B to compute A+B with OR1. The outputs of XOR1 and OR1 flow in the same direction alongside XOR2 to compute (A⊕B)⊕(A+B). The current through XOR2 is output as carry C. The gate is held at a constant voltage to maximize the GNR magnetoresistance.

These gates form a complete basis set and can be used to perform any cascaded logic function, such as the half adder demonstrated in FIG. 2. The circuit uses two XOR gates and one OR gate to perform the conventional logic function represented in Table 4. The spin logic half adder is shown with traditional symbols in FIG. 5 to compute the logic S=A⊕B and C=A·B. Metallic CNTs are used to connect the GNR transistors, with electrical connections between overlapping CNTs controlled by selective placement of insulation. Covalent graphene-CNT contacts can be used to form vertical wiring structures for large-scale integration. This allows for connections to V+ and V− in addition to input and output signals from the user. Furthermore, vertical stacking creates an opportunity for 3D integration. This cascaded spin logic family thus performs with three GNRs a function that can require 20 transistors with traditional CMOS.

The compactness of this logic family can be increased further through the use of wired-OR gates. As the magnitude of the currents determines the digital states, an OR gate can be executed by simply merging two CNT currents.

Figure 3:
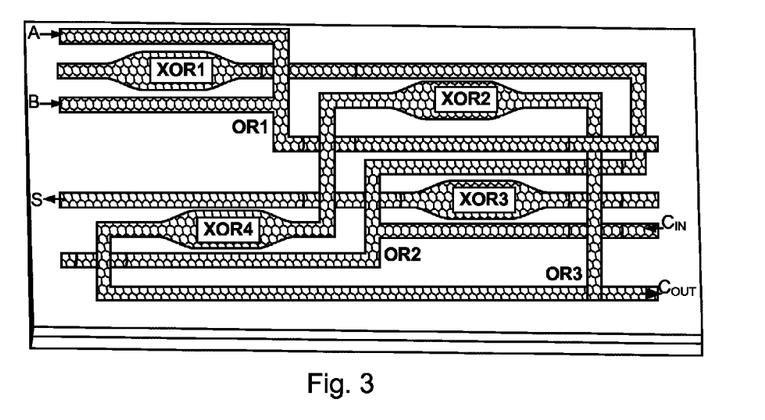
FIG. 3 is an exemplary representation of a full adder with spin logic.

FIG. 3 is an exemplary representation of a full adder with spin logic. Four XOR gates and three wired OR gates compute the full adder function. Electrical connections between green overlapping CNTs create OR gates, while brown CNTs denote insulation as in FIG. 2. A compact full adder circuit is shown with only four GNR transistors in FIG. 3, representing about an 86% decrease in device count compared to traditional CMOS. Specialized functions that rely heavily on XOR gates, such as parity generators, can utilize as few as one-tenth the devices required in CMOS.

Figure 4:
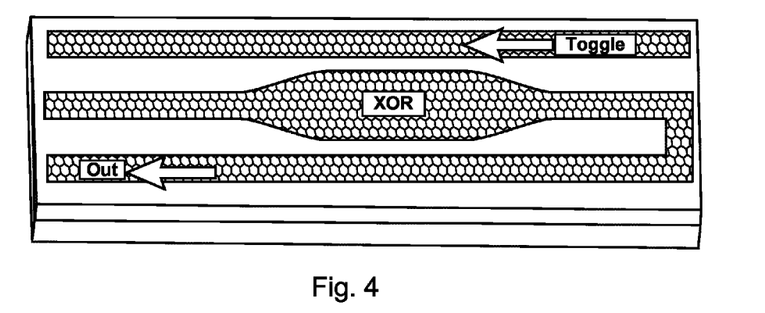
FIG. 4 is an exemplary spin logic toggle flip-flop.

In addition to logic, memory storage can also be achieved efficiently with spin logic. FIG. 4 is an exemplary spin logic toggle flip-flop. The current through the XOR GNR transistor flows through a control CNT. Therefore, when no current flows through the Toggle input, the control CNT continually reinforces the GNR state. When the Toggle input pulses a "1," the value stored in the Toggle flip-flop is inverted and maintained once the Toggle current is removed.

The toggle flip-flop memory operation is shown in truth Table 3.

TABLE 3

Toggle Flip-Flop Truth Table

| Toggle | Out | $Out_{NEXT}$ |
|---|---|---|
| 0 | 0 | 0 |
| 0 | 1 | 1 |
| 1 | 0 | 1 |
| 1 | 1 | 0 |

A toggle flip-flop, illustrated in FIG. 4, includes a single XOR gate that uses its own output as a control wire. When the Toggle input is "0," the Out value is maintained. A quickly pulsed assertion of Toggle switches the value stored in Out, as detailed in Table 3. The circuit maintains its state until switched, and can therefore be used for memory.

These circuits can be implemented with other materials exhibiting high conductivity and negative magnetoresistance. The properties of CNTs and GNRs make them candidates for use in this logic family. High performance circuits operating with clock frequencies of about 2 THz can be realized, corresponding to worst-case switching times of about 500 fs. The energy-delay product for each gate, a metric of computing efficiency, can be determined for spin logic as $EDP = Pt_d^2 \approx 6.8 \times 10^{-28}$ Js. As the gates in the spin logic family perform the functionality of between four and twelve CMOS transistors, spin logic can be approximately 100 times more efficient than 22 nm CMOS.

Spin logic permits the development of cascaded spintronic logic circuits composed solely of low-dimensional carbon materials, resulting in compact circuits with reduced area that are far more efficient than CMOS. By using the characteristics of GNRs and CNTs, spin logic opens a pathway to systems and methods for the next generation of high performance computing.

An implementation includes the following:

Circuit parameters. Spin logic circuits can include parallel CNTs with length $l_{cnt}=400$ nm and radius $r_{cnt}=3$ nm, of which sections are unzipped to form GNRs with length $l_{gnr}=50$ nm and width $w_{gnr}=2\pi r_{cnt} \approx 19$ nm. The unzipped GNR sections are separated from neighboring CNTs by a distance d=5 nm. The differential supply voltage is $V_{supply}=V+-V-=5$ V.

Power dissipation. As the length scales are in the ballistic regime, the V+ and V− terminals are separated by an on-state series resistance $R_{total}=2R_{cnt}+R_{gnr} \approx 2 \cdot 650\ \Omega + 3.3\ k\Omega \approx 4.6\ k\Omega$ for 10-wall CNTs[6,29]. The on-state current $I_{on}=V/R_{total} \approx 1.1$ mA. The off-state current flow $I_{off}$ is negligible due to a significantly higher resistance. By Ampere's Law, the on-state current through a CNT creates a magnetic field through a neighboring GNR $B=\mu_o I_{on}/2\pi d = 0.044$ T, sufficient to activate the GNR magnetoresistance. The average power dissipation per logic gate $P=V_{supply}I_{average}=V_{supply}(I_{on}+I_{off})/2 \approx 2.7$ mW.

Switching time. The spin logic switching time $t_d=t_{mag}+t_{gnr}+t_{prop}$ is the summation of the times required for a CNT current to switch a magnetic field in a neighboring GNR ($t_{mag}$), the GNR magnetoresistance to switch in response to a magnetic field ($t_{gnr}$), and the electric field to propagate through the CNT to switch the current ($t_{prop}$). The propagation time $t_{prop}$ is significantly larger than $t_{mag}$ and $t_{gnr}$, and therefore determines $t_d$. The electromagnetic wave propagation speed in a CNT is $v_f=1/\sqrt{L_K C_Q}=800$ km/s, where $L_K=400$ pH/nm is the kinetic inductance and $C_Q=0.4$ aF/nm is the quantum capacitance. The worst-case logic gate switching time can be $t_d=t_{prop}=l_{ent}/v_f=500$ fs.

Figure 5:
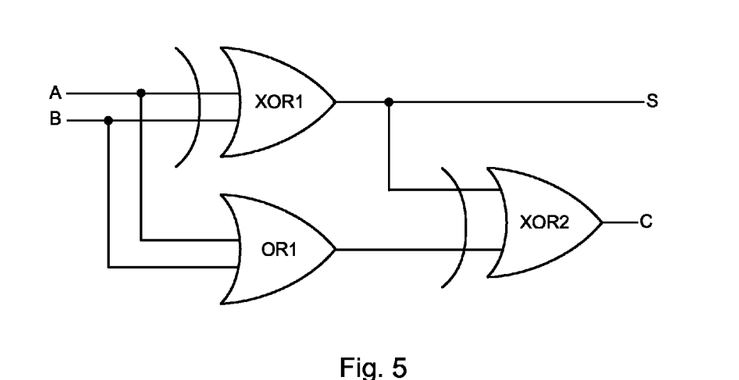
FIG. 5 is an exemplary symbolic schematic representation of a spin logic half adder.

FIG. 5 is symbolic schematic representation of an spin logic half adder. Shown here with conventional symbols, the spin logic one-bit half adder uses inputs A and B are input to XOR1 to compute S=A⊕B, and to OR1 to compute A+B. XOR2 performs the XOR function on A⊕B and A+B to calculate C=(A⊕B)⊕(A+B), which is equivalent to C=A·B.

A half adder truth table for the embodiment of FIG. 5 is presented as Table 4.

TABLE 4

Half Adder Truth Table

| A | B | S | C |
|---|---|---|---|
| 0 | 0 | 0 | 0 |
| 0 | 1 | 1 | 0 |
| 1 | 0 | 1 | 0 |
| 1 | 1 | 0 | 1 |

Figure 6:
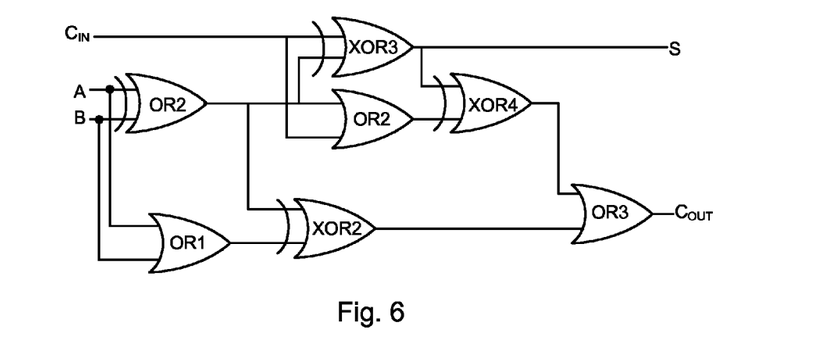
FIG. 6 is an exemplary symbolic schematic representation of a spin logic full adder.

FIG. 6 is an exemplary spin logic full adder shown in a schematic symbolic implementation. The spin logic full adder uses two half adders to compute the full adder function. Shown here with conventional symbols, the output of XOR1, which is equivalent to the S value from the half adder, is used as an input to OR2 and XOR3 along with $C_{IN}$. The full adder S output is then computed as S=$C_{IN}$⊕(A⊕B). OR2 outputs $C_{IN}$+(A⊕B), which is used along with S as an input to XOR4 to compute ($C_{IN}$+(A⊕B))⊕($C_{IN}$⊕(A⊕B)). This output of XOR4 is equivalent to A·$C_{IN}$+B·$C_{IN}$. OR3 takes this signal as an input along with the output of XOR2, which is equivalent to the C value from the half adder, to compute $C_{OUT}$=A·B+A·$C_{IN}$+B·$C_{IN}$.

A full adder truth table is presented herein as Table 5.

TABLE 5

Full Adder Truth Table

| A | B | $C_{IN}$ | S | $C_{OUT}$ |
|---|---|---|---|---|
| 0 | 0 | 0 | 0 | 0 |
| 0 | 0 | 1 | 1 | 0 |
| 0 | 1 | 0 | 1 | 0 |
| 0 | 1 | 1 | 0 | 1 |
| 1 | 0 | 0 | 1 | 0 |
| 1 | 0 | 1 | 0 | 1 |
| 1 | 1 | 0 | 0 | 1 |
| 1 | 1 | 1 | 1 | 1 |

While a half adder can be used for the first bit of binary addition, addition of the other bits requires an extra input: the carry value from the previous bit, $C_{IN}$. The sum S and carry-out $C_{OUT}$ are calculated based on those three inputs as shown in the truth Table 5.

Figure 7:
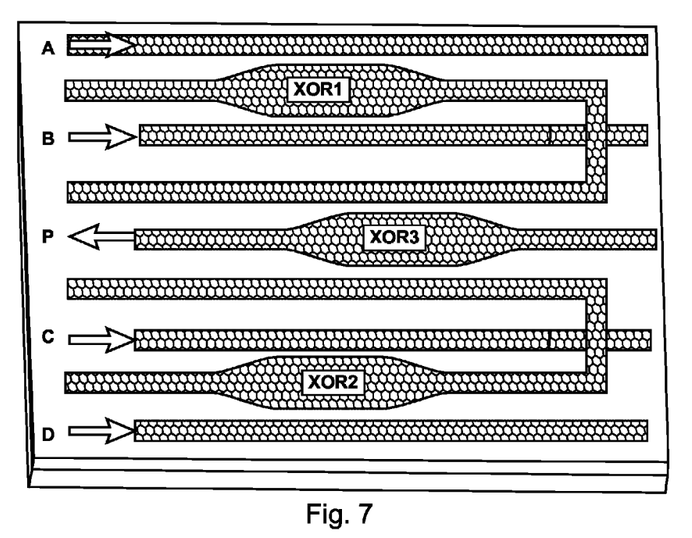
FIG. 7 is an exemplary simplified schematic representation of a spin logic parity gate.

FIG. 7 is an exemplary simplified schematic representation of an spin logic parity gate. The parity gate, used in error detection and correction, computes P=(A⊕B)⊕(C⊕D)= A⊕B⊕C⊕D. Thus, when there is an odd number of "1" inputs, the output is "1;" the output is "0" if there are an even number of "1" inputs.

Figure 8:
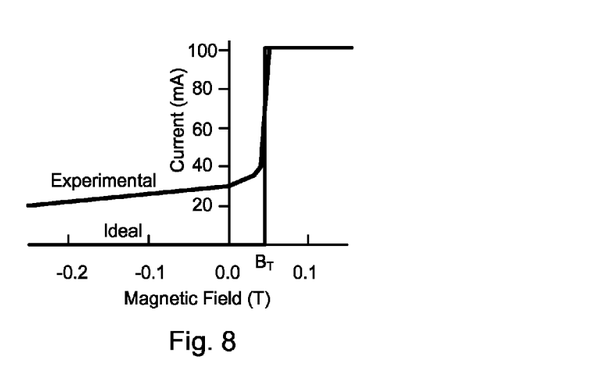
FIG. 8 is an exemplary spin diode characteristics.

FIG. 8 is an exemplary spin diode I-B characteristic. The bilayer avalanche spin-diode with Vbias=10.30 V can exhibit nearly ideal behavior, but has a finite "off" resistance and gradual switching. Spintronics is a possible foundation for a next generation of computers in which logical switching is performed through control of electron spin. The above-described spin-diode logic family can be applied to the bilayer avalanche devices. The graphene nanotubes can be replaced with an indium/antimony (InSb) p-type semiconductor/n-type conductor (p-n) bilayer channel avalanche spin-diode. The magnetic analog of an electrical diode is shown in FIG. 8. The application of an external magnetic field greater than the spin-diode threshold BT switches the spin-diode from a resistive to a conductive state. BT is tuned through control of the voltage Vbias applied across the device. Other semiconductor materials can be used.

Figure 9:
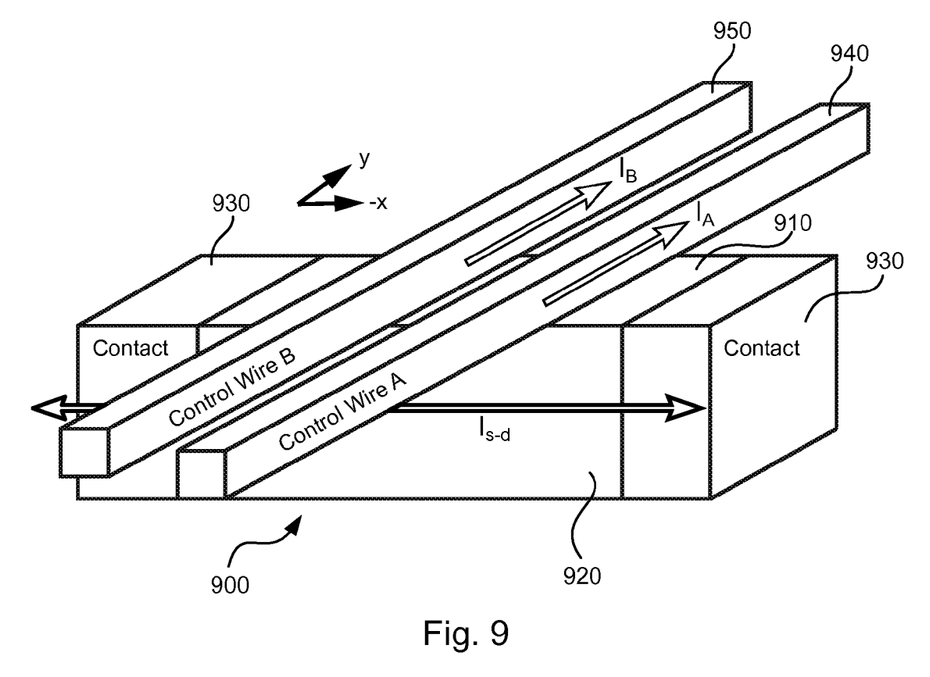
FIG. 9 is an exemplary bilayer avalanche spin-diode basis logic gate.

FIG. 9 is an exemplary bilayer avalanche spin-diode basis logic gate. A spintronic computing system and method is described in which InSb p-n bilayer avalanche spin-diodes 900 can be cascaded to efficiently perform complex logic operations. The InSb p-n bilayer avalanche spin-diodes 900 can include an n-type material 910 and a p-type material 920, and contacts 930. This spin-diode logic family uses control wires, e.g., control wire A 940 and control wire B 950, to generate magnetic fields that modulate the resistance of the spin-diodes 900, and currents through the devices control the resistance of cascaded devices. This cascading scheme permits compact logic circuits with switching speeds determined by electromagnetic wave propagation rather than electron motion, enabling high-performance spintronic computing.

The InSb p-n bilayer channel avalanche spin-diodes 900 are used as the magnetoresistive switching elements for the spin-diode logic family. Spin-diode logic, e.g., as used for InAs/InMnAs heterojunctions, is applicable to any two-terminal magnetoresistive device that functions as a spin-diode. In the logic family, a constant bias voltage Vbias is applied to spin-diodes, and the current through the spin-diodes is modulated by magnetic fields created by control wires. Binary logic states are represented by the spin-diode currents as state variables: large currents Ihigh resulting from magnetic fields greater than the threshold BT are a logical '1', and small currents Ilow from fields below BT are a logical '0'. The currents through the spin-diodes are routed through the control wires of other spin-diodes to manipulate their magnetoresistance. The cascading technique allows for the creation of the complex circuits required for computing.

In one implementation, a structure of the control wire and bilayer avalanche spin-diode is shown in FIG. 9. Current in the y-direction through the two control wires creates a magnetic field B in the x-direction, parallel to the plane of the channel, $$B = \frac{\mu I_A}{2\pi r}\hat{x} + \frac{\mu I_B}{2\pi r}\hat{x} = K(I_A + I_B)\hat{x}, \quad (1)$$

where μ is the spin-diode permeability, r is the distance from the control wire to the magnetoresistive region, and IA and IB are the currents through the control wires (positive current determined in the ŷ direction). For simplicity, use $$K = \frac{\mu}{2\pi r},$$

with units of $$\frac{T}{A},$$

to refer to the geometry-dependent proportionality constant. Vbias is chosen such that $$2KI_{low} < B_T < \kappa(I_{high} - I_{low}) \quad (2)$$

$$I_{s-d} = \begin{cases} I_{high}, & B_x > B_T \\ I_{low}, & B_x < B_T \end{cases} \quad (3)$$

guaranteeing correct spin-diode current Is-d for any combination of input currents Ilow and Ihigh. The current can be limited to ensure a single value for Ihigh and to prevent damage to the spin-diodes.

When the control wires 940, 950 are biased in the same direction, the magnetic fields created by IA and IB are additive. When B=1, IB=Ihigh, creating a net magnetic field through the spin-diode Bx>BT for any positive value of IA. Therefore, irrespective of A, Is–d=Ihigh whenever B=1. When A=B=0, IA=IB=Ilow and Bx=2κIlow, determined in equation (2) to be less than BT, resulting in Is–d=Ilow. As IA increases to Ihigh, Bx surpasses BT, causing Is–d to switch to Ihigh. The electrical and magnetic responses to binary digital inputs are listed in the truth table of Table 6, demonstrating functionality equivalent to the logical OR function, $F = A \land B$.

TABLE 6

OR GATE TRUTH TABLE

| A | $I_A$ | B | $I_B$ | B | F | $I_{s-d}$ |
|---|---|---|---|---|---|---|
| 0 | $I_{low}$ | 0 | $I_{low}$ | $2KI_{low}$ | 0 | $I_{low}$ |
| 0 | $I_{low}$ | 1 | $I_{high}$ | $K(I_{high} + I_{low})$ | 1 | $I_{high}$ |
| 1 | $I_{high}$ | 0 | $I_{low}$ | $K(I_{high} + I_{low})$ | 1 | $I_{high}$ |
| 1 | $I_{high}$ | 1 | $I_{high}$ | $2KI_{high}$ | 1 | $I_{high}$ |

Biasing the control wires 940, 950 in opposite directions causes the fields to counteract. As shown in Table 7, this function is equivalent $F = A \land \overline{B}$, an AND gate with one inverted input, referred to as "IAND."

TABLE 7

IAND GATE TRUTH TABLE

| A | $I_A$ | B | $I_B$ | B | F | $I_{s-d}$ |
|---|---|---|---|---|---|---|
| 0 | $I_{low}$ | 0 | $-I_{low}$ | 0 | 0 | $I_{low}$ |
| 0 | $I_{low}$ | 1 | $-I_{high}$ | $-K(I_{high} - I_{low})$ | 0 | $I_{low}$ |
| 1 | $I_{high}$ | 0 | $-I_{low}$ | $K(I_{high} - I_{low})$ | 1 | $I_{high}$ |
| 1 | $I_{high}$ | 1 | $-I_{high}$ | 0 | 0 | $I_{low}$ |

The OR and IAND functions make up the basis gate set of this bilayer avalanche spin-diode logic family. With this basis set, Boolean logic functions can be performed. The logic gates can be cascaded directly, without any additional control or amplification circuitry.

Figure 10:
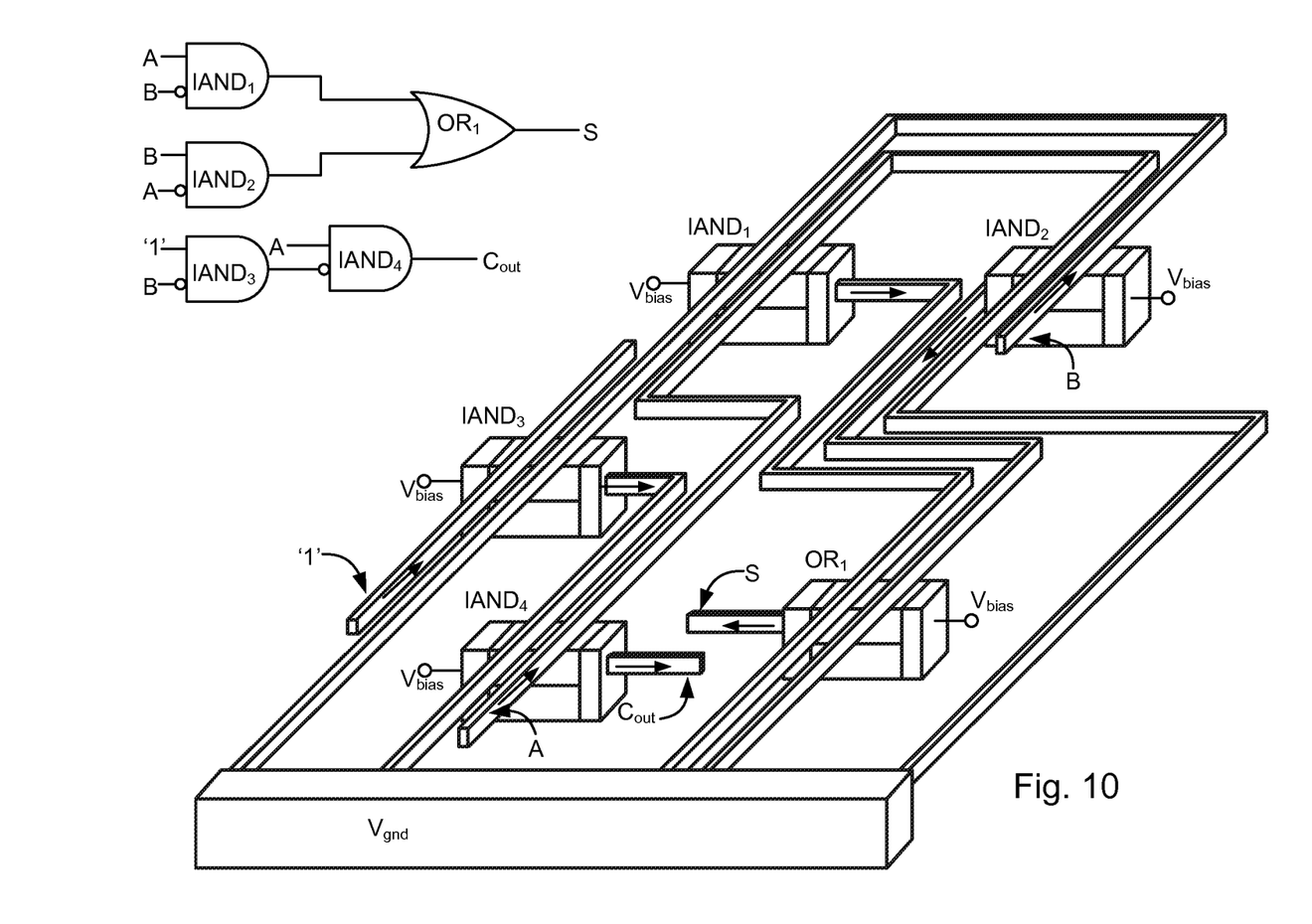
FIG. 10 is an exemplary avalanche spin-diode logic one-bit half adder.

FIG. 10 is an exemplary avalanche spin-diode logic one-bit half adder. A is an input to the spin-diodes labeled IAND1, IAND2, and IAND4, and B is an input to IAND1, IAND2, and IAND3. The outputs of IAND1 and IAND2 are the inputs for OR1, which produces S. Similarly, Cout is determined by IAND4, which receives as inputs A and the output of IAND3, which in turn receives B and a constant Ihigh as inputs. As a demonstration of the application of the spin-diode logic family to bilayer channel spin-diodes, the one-bit half adder in FIG. 10 determines, e.g., calculates, the binary addition of two input bits (A and B) to generate a sum (S) and carry-out (Cout) bit. The circuit computes the half adder function optimized for bilayer avalanche spin-diode logic as:

$$S = A \oplus B = (A \land \overline{B}) \lor (B \land \overline{A}) \quad (4)$$

$$C_{out} = A \land B = A \land \overline{1 \pm B} \quad (5)$$

using only five spin-diodes. In general, the logic family requires fewer than half the number of active devices in CMOS, with several representative examples in Table 8.

TABLE 8

Logical Efficiency Comparison

| Logic Function | CMOS Device Count | Bilayer Avalanche Spin-Diode Logic Device Count |
|---|---|---|
| Half Adder | 16 | 5 |
| Full Adder | 28 | 11 |
| 2:1 MUX | 12 | 4 |
| SR Latch | 8 | 2 |

Electromagnetic wave propagation determines the switching speed in bilayer avalanche spin-diode logic, enabling high-performance computing. Whereas the RLC interconnect delay is a growing problem in conventional integrated systems such as CMOS in which voltage is the state variable [20], charge transfer and accumulation is not a component of the switching process for systems in which current is the state variable. The complete switching delay in spin-diode logic, $$t_d = t_{mag} + t_{sd} + t_{prop}, \quad (6)$$

is the summation of the times for a control wire current to switch a magnetic field in a neighboring spin-diode (tmag), the spin-diode magnetoresistance to switch in response to a magnetic field (tsd), and the electric field to propagate through the control wire to switch the current (tprop). The speeds of the three phenomena are on the order of the speed of light, permitting much higher performance than available in the best modern processors.

Furthermore, the fast operation need not result in excessive power consumption. In spin-diode logic, power consumption is primarily a result of the constant flow of current through the spin-diodes, with minimal additional power consumed during the switching process. Assuming a random distribution of signal values in a processor, the power dissipation is $$P = P_{dynamic} + P_{static} \approx P_{static} = \frac{(I_{high} - I_{low})}{2} V_{bias} \quad (7)$$

The power is proportional to the voltage bias and current, which may be reduced through scaling of the diode dimensions, and is nearly independent of operating frequency. This behavior is in contrast to CMOS, in which power consumption in an ideal system is proportional to the operating frequency. In modern CMOS systems, the parasitic leakage power can also poses a problem.

Variations to the logic structure described herein are possible. First, device count reductions are possible with a wired OR gate due to the use of current as the state variable. The use of a second Vbias applied to some spin-diodes can result in a negative BT, supplementing the set of basis logic gates. Additionally or alternatively, more than two control wires may be used, further increasing the complexity of the functions performed by each gate. Additionally or alternatively, the control wires can be oriented to create fields in the perpendicular direction, triggering the positive magnetoresistance. Logic circuit designs for such devices can be implemented, e.g., as described above.

Bilayer channel spin-diode logic efficiently computes complex logic functions, providing a feasible solution to the challenge of cascading the nearly ideal room temperature spin-diodes. The small changes in magnetic field allows for spintronic switching with Amperian fields, allowing for spintronic switching speeds dependent on electromagnetic wave propagation and faster than those possible through spin-transfer torque. The high performance and compact circuits achieved in bilayer avalanche spin-diode logic can open a spintronic pathway to a next generation of computing In accordance with the embodiments, a spintronic logic family of graphene nanoribbon (GNR) transistors and metallic carbon nanotube (CNT) interconnect are described that achieve high-performance logic circuits. The cascaded logic gates are accomplished by using the output currents of graphene nanoribbon (GNR) transistors to create magnetic fields through other GNRs that cause incoherent spintronic switching. The logic family can exploit the negative magnetoresistance recently predicted and discovered in GNR transistors to differentiate clearly between binary states. The material properties of carbon-based materials in concert with this novel logic family allow for Terahertz operation and permit a roughly 100× decrease in energy-delay product compared to CMOS.

Manipulation of the spin-degree of freedom for spintronic computing utilize logic families that harness the unique mechanisms of spintronic switching devices. Cascading, one device directly driving another device, has been well known as a major challenge and requirement of a logic family since John Von Neumann's 1945 proposal for a stored-program electronic computer. If the input and output signals are not of the same type and magnitude, it is difficult to connect devices without an additional device for translation. This extra device can consume power, time, and area, and severely degrade the utility of the logic family. Few spintronic logic families have demonstrated cascaded circuits, with notable exceptions.

Recent advances in CNT unzipping mechanisms and exceptional negative magnetoresistance in GNRs and partially unzipped CNTs permit the development of a spintronic logic family. Under a constant gate voltage, the application of a magnetic field normal to the device plane can cause the current through a GNR transistor to be increased by a factor of greater than 10,000 at cryogenic temperatures. This phenomenon may occur due to a decrease in cyclotron radius caused by the magnetic field, resulting in increased conduction through the nanoribbon.

Accordingly, systems and methods for computing are described herein for spin logic. This logic family exploits the characteristics of graphene to perform efficient high-performance computing using only low-dimensional carbon materials. The GNR transistors, in concert with metallic CNT interconnect, provide compact logic, low current requirements, and fast switching times.

The systems and methods include logic computation using carbon nanotubes and graphene nanoribbons in a spin logic circuit structure. This logic family exploits the nearly 100% negative magnetoresistance recently observed in graphene nanoribbon transistors to accomplish spintronic switching. By using the output currents of the graphene nanoribbon transistors to create magnetic fields through other graphene nanoribbon transistors, the requirement of cascaded logic gates is achieved can be. The material properties of carbon-based materials in concert with this efficient logic family permit high-performance computing with minimal power dissipation.

This systems and methods also include an application of an existing device, the graphene nanoribbon field-effect transistor. Unlike conventional applications of field-effect transistors, in which gate voltage is used to manipulate switching characteristics, the systems and methods can keep the gate voltage constant and use magnetic fields to manipulate switching characteristics. In some embodiments, current is supplied to the graphene nanoribbon field-effect transistor by a current source.

Applications if the systems and methods include, for example, high performance computing, general computing, mobile computing, low power computing, and low temperature computing.

Advantages of the systems and methods include, for example, 2 THz clock frequency due to current-based logic and carbon material properties, potential for 100× improvement in computing efficiency compared to CMOS, cascaded logic, and high noise tolerance.

Spin logic can be structured as follows: an array of parallel CNTs is grown on an insulating substrate above a conductive gate. Short longitudinal sections of the CNT array are selectively unzipped to form GNRs that remain covalently bonded and electrically connected to the CNTs. To form logical interconnections, some CNT segments are coated with insulation to regulate crossing junction connectivity with CNTs grown in the perpendicular direction. The universal gate is held constant in order to obtain the maximum magnetoresistance of the GNR transistors. The drain and source of each transistor are connected via CNTs directly to the circuit's high and low voltages, V+ and V−, with a constant potential difference. The CNT wires making these connections are routed alongside other GNRs for cascading; the current through these wires creates a magnetic field. High control currents create large magnetic fields in the GNRs, activating the negative magnetoresistance and substantially increasing the current flow. This logic family leverages the properties of carbon materials to perform logic compactly and efficiently.

The GNR field-effect transistor is thus treated as a two-terminal device with a constant gate voltage; the additional functionality achievable through control of the gate voltage can be considered. As the conductivity of the transistor is controlled by the gate voltage and the magnetic field, this restriction on the gate voltage implies a conductivity modulated solely by applied magnetic field. Two states can thus be determined: a conductive state resulting from the application of a magnetic field through the GNR and a resistive state produced in the absence of an external magnetic field. The current through a GNR transistor in its conductive state is determined as a "1;" the resistive current is determined as a "0." Current is therefore the binary state variable and all nodes maintain constant voltages at all times.

The foregoing and other objects can be achieved which provides, in accordance with an apparatus aspect thereof, a logic switching element having a magnetoresistive element that is formed of a magnetoresistive material, and is configured to have first and second terminals. There are additionally provided first and second paramagnetic conductors disposed in proximity to the magnetoresistive element, whereby a magnetic field generated by at least one of the first and second paramagnetic conductors will affect the magnetoresistive characteristic of the magnetoresistive element.

In one embodiment, the magnetoresistive element is a negative magnetoresistive element. In an embodiment, the negative magnetoresistive element is a graphene ribbon.

In a further embodiment, at least one of the first and second paramagnetic conductors is formed of carbon. In an advantageous embodiment, at least one of the first and second paramagnetic conductors is formed of carbon nanotubes.

The negative magnetoresistive element has a determined conductivity characteristic, wherein the conductivity of the negative magnetoresistive element is increased in the presence of the magnetic field generated by at least one of the first and second paramagnetic conductors. In another embodiment, there is provided a further magnetoresistive element coupled to receive a current from the negative magnetoresistive element. The further magnetoresistive element is, in some embodiments, a further negative magnetoresistive element.

A current source is provided in some embodiments for supplying a current to the magnetoresistive element.

In operation, the voltages across the first and second terminals remains substantially independent of a change in the magnetoresistive characteristic of the magnetoresistive element in response to the magnetic fields generated by the at least one of the first and second paramagnetic conductors.

In accordance with systems and methods, there is provided operating a logic switching element by providing a graphene nanoribbon (GNR) having a determined magnetoresistive characteristic that varies in response to the presence of a magnetic field; providing first and second carbon nanotubes (CNT) control wires disposed in the vicinity of the graphene nanoribbon, the first and second carbon nanotubes wires each generating an associated magnetic field in response to an associated current flowing therethrough; controlling the determined magnetoresistive characteristic of the GNR, whereby the GNR functions in a selectable one of the following states: I) No current flows through either of the CNT control wires, whereby the magnetoresistive characteristic of the GNR corresponds to a resistive state; II) Current flows through exactly one of the CNT control wires, whereby the magnetoresistive characteristic of the GNR corresponds to a conductive state; III) Current flows through both of the CNT control wires in parallel directions and of equal magnitude, whereby the magnetic fields through the graphene layer are anti-parallel, whereby the magnetoresistive characteristic of the GNR corresponds to a resistive state; and IV) Current flows through both of the CNT control wires in anti-parallel directions, whereby the magnetic fields through the graphene layer are parallel, resulting in a doubly large magnetic field, whereby the magnetoresistive characteristic of the GNR corresponds to a conductive state.

In one embodiment of the systems and methods, the magnetoresistive characteristic of the GNR corresponds to a conductive state, the magnitude of a current that flows through the GNR is increased.

In another embodiment, providing a graphene nanoribbon includes installing the GNR on an insulating material that is grown on a metallic gate.

In yet another embodiment, providing a graphene nanoribbon includes providing a spintronic graphene nanoribbon.

In accordance with a further apparatus, there is provided a logic switching arrangement that is provided with a plurality of logic switching elements, the logic switching element having: a graphene nanoribbon (GNR) having a determined magnetoresistive characteristic that varies in response to the presence of a magnetic field; a carbon nanotube (CNT) control wire disposed in the vicinity of the graphene nanoribbon, the carbon nanotube wire generating a magnetic field in response to an associated current flowing therethrough; and an interconnection arrangement for coupling respective ones of the plurality of logic switching elements to one another to form a logic function unit.

In one embodiment, the logic function block is configured as a full adder. In another embodiment, the logic function block is configured as a half adder. In still another embodiment, the logic function block is configured a parity gate, and in yet another embodiment, the logic function block is configured as a toggle flip-flop.

In an embodiment, the plurality of logic switching elements is provided with a second carbon nanotube (CNT) control wire disposed in the vicinity of the graphene nanoribbon, the carbon nanotube wire generating a magnetic field in response to an associated current flowing therethrough.

It is to be understood that the drawing and description in this disclosure are proffered to facilitate comprehension of the embodiments, and should not be construed to limit the scope thereof Moreover, the technical effects and technical problems in the specification are exemplary and are not limiting. The embodiments described in the specification may have other technical effects and can solve other technical problems. Many modifications and other embodiments set forth herein will come to mind having the benefit of the teachings presented in the foregoing descriptions and the associated drawings. Although specific terms are employed herein, they are used in a generic and descriptive sense only and not for purposes of limitation.

The invention claimed is:

1. A logic switching element, comprising:
a magnetoresistive element, the magnetoresistive element being formed of a magnetoresistive material and having first and second terminals;
first and second conductors disposed in proximity to the magnetoresistive element, whereby a magnetic field generated by at least one of the first and second conductors will affect the magneto resistive characteristic of the magnetoresistive element, wherein the magnetoresistive element comprises a negative magnetoresistive element.

2. The logic switching element of claim 1, wherein the negative magnetoresistive element comprises a graphene ribbon.

3. The logic switching element of claim 2, wherein at least one of the first and second conductors is formed of carbon.

4. The logic switching element of claim 3, wherein at least one of the first and second conductors is formed of carbon nanotubes.

5. The logic switching element of claim 1, wherein the negative magnetoresistive element comprises an InSb p-n bilayer channel avalanche diode.

6. The logic switching element of claim 1, wherein the negative magnetoresistive element has a determined conductivity characteristic, wherein the conductivity of the negative magnetoresistive element is increased in the presence of the magnetic field generated by at least one of the first and second conductors.

7. The logic switching element of claim 1, wherein there is provided a further magnetoresistive element coupled to receive a current from the negative magnetoresistive element.

8. The logic switching element of claim 7, wherein the further magnetoresistive element is a further negative magnetoresistive element.

9. The logic switching element of claim 1, wherein there is further provided a current source for supplying a current to the magnetoresistive element.

10. The logic switching element of claim 1, wherein voltages across the first and second terminals remains substantially independent of a change in the magnetoresistive characteristic of the magnetoresistive element in response to the magnetic fields generated by the at least one of the first and second conductors.

11. A method of operating a logic switching element, comprising:
providing a graphene nanoribbon (GNR) having a determined magnetoresistive characteristic that varies in response to the presence of a magnetic field;
providing first and second carbon nanotubes (CNT) control wires disposed in the vicinity of the graphene nanoribbon, the first and second carbon nanotubes wires each generating an associated magnetic field in response to an associated current flowing therethrough;
controlling the determined magnetoresistive characteristic of the GNR whereby the GNR functions in a selectable one of the following states:
I) No current flows through either of the CNT control wires, whereby the magnetoresistive characteristic of the GNR corresponds to a resistive state;
II) Current flows through exactly one of the CNT control wires, whereby the magnetoresistive characteristic of the GNR corresponds to a conductive state;
III) Current flows through both of the CNT control wires in parallel directions and of equal magnitude, whereby the magnetic fields through the graphene layer are anti-parallel, whereby the magnetoresistive characteristic of the GNR corresponds to a resistive state;
IV) Current flows through both of the CNT control wires in anti-parallel directions, whereby the magnetic fields through the graphene layer are parallel, resulting in a doubly large magnetic field, whereby the magnetoresistive characteristic of the GNR corresponds to a conductive state.

12. A logic switching arrangement, comprising:
a plurality of logic switching elements, each logic switching element having:
a resistive element having a determined magnetoresistive characteristic that varies in response to the presence of a magnetic field;
a control wire disposed in the vicinity of the resistive element, the control wire generating a magnetic field in response to an associated current flowing therethrough; and
an interconnection arrangement for coupling respective ones of the plurality of logic switching elements to one another to form a logic function block, where the logic function block comprises a parity gate or a toggle flip-flop.

13. The logic switching arrangement of claim 12, wherein the logic function block comprises a full adder.

14. The logic switching arrangement of claim 12, wherein the logic function block comprises a half adder.

15. The logic switching arrangement of claim 12, wherein each of the plurality of logic switching elements is provided with a second control wire disposed in the vicinity of the graphene nanoribbon, the carbon nanotube wire generating a magnetic field in response to an associated current flowing therethrough.

16. The logic switching arrangement of claim 12, wherein the control wire comprises a carbon nanotube.

17. The logic switching arrangement of claim 12, wherein the resistive element comprises a graphene nanoribbon.

18. The logic switching arrangement of claim 12, wherein the resistive element comprises an InSb p-n bilayer channel avalanche diode.

\* \* \* \* \*